United States Patent
Katkar

(10) Patent No.: US 10,524,833 B2
(45) Date of Patent: Jan. 7, 2020

(54) DEVICE AND METHODS FOR PRECISE CONTROL OF MEDICAL PROCEDURES

(71) Applicant: Amol Suryakant Katkar, San Antonio, TX (US)

(72) Inventor: Amol Suryakant Katkar, San Antonio, TX (US)

(73) Assignee: FNAPEN LLC, San Antonio, TX (US)

(*) Notice: Subject to any disclaimer, the term of this patent is extended or adjusted under 35 U.S.C. 154(b) by 627 days.

(21) Appl. No.: 15/033,246

(22) PCT Filed: Nov. 3, 2014

(86) PCT No.: PCT/US2014/063704
§ 371 (c)(1),
(2) Date: Apr. 29, 2016

(87) PCT Pub. No.: WO2015/066621
PCT Pub. Date: May 7, 2015

(65) Prior Publication Data
US 2016/0270818 A1    Sep. 22, 2016

Related U.S. Application Data

(60) Provisional application No. 61/899,352, filed on Nov. 4, 2013.

(51) Int. Cl.
*A61B 17/34* (2006.01)
*A61B 90/00* (2016.01)

(52) U.S. Cl.
CPC .......... *A61B 17/3494* (2013.01); *A61B 90/06* (2016.02); *A61B 2090/062* (2016.02); *A61B 2217/005* (2013.01)

(58) Field of Classification Search
CPC . A61B 17/3494; A61B 10/0283; A61B 90/06; A61B 2090/062
See application file for complete search history.

(56) References Cited

U.S. PATENT DOCUMENTS

| 4,697,600 A | 10/1987 | Cardenas et al. |
| 4,766,907 A | 8/1988 | De Groot et al. |

(Continued)

FOREIGN PATENT DOCUMENTS

| EP | 0983021 | 3/2000 |
| EP | 0983749 | 3/2000 |
| WO | WO 2015/066621 | 5/2015 |

OTHER PUBLICATIONS

International Search Report and Written Opinion issued in International Patent Application No. PCT/US2014/063704 dated Feb. 13, 2015.

*Primary Examiner* — Daniel L Cerioni
*Assistant Examiner* — Raymond P Dulman
(74) *Attorney, Agent, or Firm* — Parker Highlander PLLC

(57) ABSTRACT

A device for fine needle aspiration comprising: an inner tubular member; an outer tubular member disposed around the inner tubular member, wherein the outer tubular member comprises a plurality of slots; an outer housing disposed around the outer tubular member; a biasing member disposed between the outer tubular member and the outer housing. The device also comprises a rod coupled to the inner tubular member, where the rod extends through the outer tubular member and the rod is configured to be moved from a first slot in the plurality of slots to a second slot in the plurality of slots.

18 Claims, 2 Drawing Sheets

(56) References Cited

U.S. PATENT DOCUMENTS

| | | | | |
|---|---|---|---|---|
| 4,813,940 | A | * | 3/1989 | Parry .................. A61M 5/283 604/198 |
| 4,894,055 | A | * | 1/1990 | Sudnak ............... A61M 5/3271 604/110 |
| 4,911,693 | A | * | 3/1990 | Paris .................. A61M 5/3271 604/192 |
| 5,036,860 | A | | 8/1991 | Leigh et al. |
| 5,591,138 | A | | 1/1997 | Vaillancourt |
| 5,611,778 | A | * | 3/1997 | Brinon .................. A61M 25/01 604/117 |
| 5,795,336 | A | * | 8/1998 | Romano ............. A61M 5/3271 604/110 |
| 5,916,175 | A | | 6/1999 | Bauer |
| 5,951,489 | A | | 9/1999 | Bauer |
| 6,402,701 | B1 | | 6/2002 | Kaplan et al. |
| 6,884,237 | B2 | * | 4/2005 | Asbaghi ............... A61M 5/3272 604/192 |
| 6,926,697 | B2 | * | 8/2005 | Malenchek ......... A61M 5/3272 604/197 |
| 7,037,276 | B2 | | 5/2006 | Sayet et al. |
| 7,727,190 | B2 | * | 6/2010 | Miller ................ A61M 5/3257 604/110 |
| 7,766,843 | B2 | | 8/2010 | Voegele |
| 7,798,995 | B2 | | 9/2010 | Yue et al. |
| 7,927,288 | B2 | | 4/2011 | Gianchandani |
| 8,075,522 | B2 | * | 12/2011 | Larsen .................. A61M 5/326 604/110 |
| 8,192,407 | B2 | * | 6/2012 | Pessin .................. A61M 5/3202 604/192 |
| 2002/0082518 | A1 | | 6/2002 | Weiss |
| 2003/0187400 | A1 | * | 10/2003 | Liao .................... A61M 5/3234 604/195 |
| 2003/0225430 | A1 | * | 12/2003 | Schraga ............. A61B 5/15019 606/182 |
| 2004/0220497 | A1 | * | 11/2004 | Findlay ............... A61B 10/025 600/562 |
| 2005/0090765 | A1 | | 4/2005 | Fisher |
| 2005/0228312 | A1 | | 10/2005 | Surti |
| 2009/0112119 | A1 | | 4/2009 | Kim |
| 2010/0168766 | A1 | * | 7/2010 | Zeng .................. A61B 17/3403 606/130 |
| 2011/0132420 | A1 | * | 6/2011 | Livacich ............... E04H 15/001 135/123 |
| 2012/0265156 | A1 | * | 10/2012 | Devereux ............... A61M 5/46 604/263 |
| 2013/0018311 | A1 | * | 1/2013 | Denning ............. A61M 5/2429 604/110 |
| 2013/0060160 | A1 | | 3/2013 | Heier |
| 2013/0165815 | A1 | | 7/2013 | Zinn |
| 2013/0172777 | A1 | | 7/2013 | Kwon |
| 2013/0184732 | A1 | * | 7/2013 | Tanaka .................. A61B 10/04 606/185 |

\* cited by examiner

DEVICE AND METHODS FOR PRECISE CONTROL OF MEDICAL PROCEDURES

CROSS-REFERENCE TO RELATED APPLICATION

This application is a national phase application under 35 U.S.C. § 371 of International Application No. PCT/US2014/063704, filed Nov. 3, 2014, which claims priority to U.S. Provisional Patent Application Ser. No. 61/899,352, filed Nov. 4, 2013, the contents of each of which are incorporated by reference herein.

BACKGROUND INFORMATION

Several factors can affect a sample yield during a fine needle aspiration (FNA). For example, the amount of sample obtained from FNA procedures can depend on several qualities of excursions including the velocity, the total number of excursions, and the depth of the excursion.

Existing systems and methods for FNA procedures can lead to inconsistent results due to variations in these qualities and other factors.

Accordingly, there exists a need for devices and methods to provide precise, accurate FNA procedures to increase the quality of sample yields.

SUMMARY

Exemplary embodiments of the present disclosure comprise a device configured to allow a user to precisely control the depth of penetration of instruments used during medical procedures, including for example fine needle aspiration (FNA). With typical FNA procedures, it is difficult for a user to control the motion of their fingers and wrists in order to get an adequate specimen. This can result in a failed FNA procedure, leading to patient frustration and repeated attempt which can increase the cost of the procedure (in both time and money) to the patient, physician, and institute. In addition, lack of instrument control can lead to poor samples contaminated by blood which are not suitable for analysis.

As explained more fully below, embodiments of the present disclosure can allow a user to increase the speed and depth of the instrument penetration during FNA or other procedures. This can increase the amount of tissue taken during the sample and decrease the contamination of the sample by blood.

Certain embodiments include a device for fine needle aspiration comprising: an inner tubular member comprising a proximal end and a distal end; an outer tubular member disposed around the inner tubular member, where the outer tubular member comprises a proximal end, a distal end, and a plurality of slots; an outer housing disposed around the outer tubular member, where the outer housing comprises a proximal end and a distal end; a biasing member disposed between the outer tubular member and the outer housing; and a rod coupled to the inner tubular member. In particular embodiments: the rod extends through the outer tubular member; the rod is configured to be moved from a first slot in the plurality of slots to a second slot in the plurality of slots; the first slot is a first distance from proximal end of the housing; the second distance from the proximal end of the housing; and the biasing member is configured to bias the housing away from the rod.

In specific embodiments, the rod is coupled to the inner tubular member via a collar that extends around the inner tubular member. In certain embodiments, the collar is configured for axial and radial sliding engagement with the inner tubular member. In particular embodiments, the outer tubular member comprises a projection that engages the biasing member. In some embodiments, the proximal end of the housing is configured to engage the projection when the biasing member is in an expanded configuration, and the proximal end of the housing is configured to engage the rod when the biasing member is in a compressed configuration.

In specific embodiments, the outer tubular member extends a first distance from the distal end of the outer housing when the biasing member is in an expanded configuration; the outer tubular member extends a second distance from the distal end of the outer housing when the biasing member is in a compressed configuration; and the first distance is less than the second distance.

In certain embodiments, the distal end of the outer tubular member comprises a coupling mechanism configured to be coupled to a needle. In particular embodiments, the proximal end of the outer tubular member comprises a port configured to be coupled to a vacuum source. In some embodiments, the coupling mechanism and the port are in fluid communication with the outer tubular member and the inner tubular member. In specific embodiments, the biasing member is configured as a coil spring that extends around the outer tubular member.

In certain embodiments, the plurality of slots comprises a plurality of radial slots each at a different distance from the proximal end of the outer tubular member and wherein the plurality of radial slots are coupled via a longitudinal slot. In particular embodiments, when the biasing member is in an expanded configuration the plurality of radial slots comprise: a first slot positioned approximately 0.5 cm from the proximal end of the outer housing; a second slot positioned approximately 1.0 cm from the proximal end of the outer housing; a third slot positioned approximately 2.0 cm from the proximal end of the outer housing; a fourth slot positioned approximately 3.0 cm from the proximal end of the outer housing; and a fifth slot positioned approximately 4.0 cm from the proximal end of the outer housing.

Certain embodiments include a method of performing a fine needle aspiration, the method comprising: obtaining a device for fine needle aspiration comprising: an inner tubular member comprising a proximal end and a distal end; an outer tubular member disposed around the inner tubular member, where the outer tubular member comprises a proximal, a distal end, and a plurality of slots; an outer housing disposed around the outer tubular member, where the outer housing comprises a proximal end and a distal end; a biasing member disposed between the outer tubular member and the outer housing; and a rod coupled to the inner tubular member, and where: the rod extends through the outer tubular member; the rod is configured to be moved from a first slot in the plurality of slots to a second slot in the plurality of slots; the first slot is a first distance from proximal end of the housing; the second slot is a second distance from the proximal end of the housing; and the biasing member is configured to bias the housing away from the rod. In particular embodiments the method includes coupling a needle to a coupling mechanism located near the distal end of the outer tubular member; placing the rod in a desired slot of the plurality of slots, wherein a distance from the desired slot to the proximal end of the outer housing is equivalent to a desired distance of penetration of the needle; placing the needle against a surface of a patient; moving the proximal end of the outer tubular member toward the outer housing until the rod engages the proximal end of the outer housing, thereby penetrating the surface of the patient with the needle to a desired distance of penetration; and withdrawing the needle from the patient.

In some embodiments, the desired distance of penetration is approximately 0.5 cm. In specific embodiments, the desired distance of penetration approximately 1.0 cm. In certain embodiments, the desired distance of penetration approximately 2.0 cm. In particular embodiments, the desired distance of penetration approximately 3.0 cm. In certain embodiments, the desired distance of penetration approximately 4.0 cm.

In particular embodiments, placing the rod in the desired slot comprises: moving the rod in a first radial direction toward a longitudinal slot; moving the rod within the longitudinal slot toward the desired slot; and moving the rod in a second radial direction into the desired slot.

In some embodiments, moving the proximal end of the outer tubular member toward the outer housing comprises overcoming a force exerted by the biasing mechanism on the outer housing and the outer tubular member.

In the following disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DETAILED DESCRIPTION OF ILLUSTRATIVE EMBODIMENTS

Figure 1:
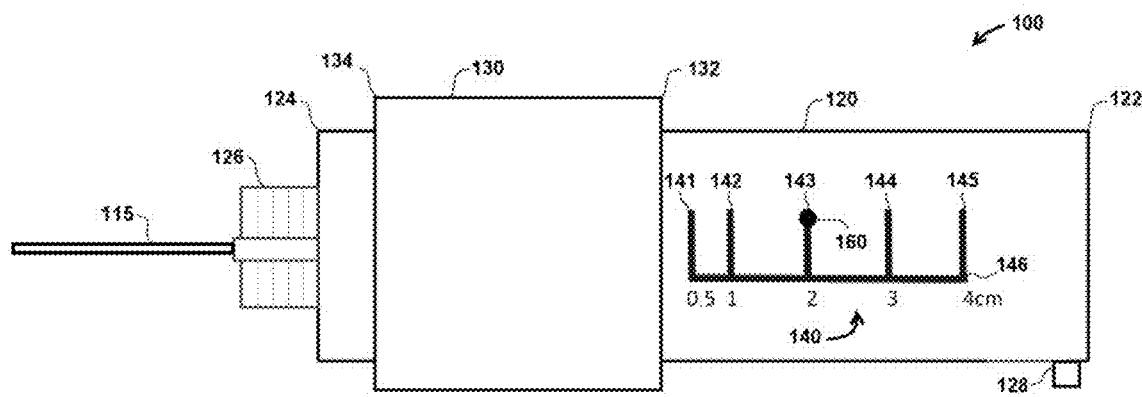
FIG. 1 is a top view of an exemplary embodiment of the present disclosure.
Figure 2:
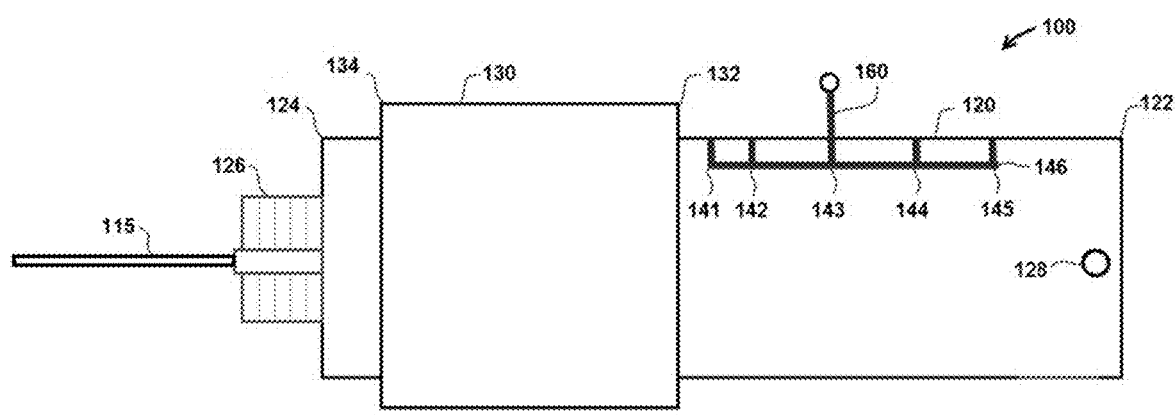
FIG. 2 is a side view of the embodiment of FIG. 1.

Referring to FIGS. 1-4, an exemplary embodiment of a device 100 configured for fine needle aspiration device comprises an inner tubular member 110, an outer tubular member 120 comprising a plurality of slots 140, an outer housing 130, and a biasing member 150. In the embodiment shown, outer tubular member 120 is disposed around inner tubular member 110 and biasing member 150 is disposed between outer tubular member 120 and outer housing 130.

In this embodiment, inner tubular member 110 comprises a proximal end 112 and a distal end 114, outer tubular member 120 comprises a proximal end 122 and a distal end 124, and outer housing 130 comprises a proximal end 132 and a distal end 134. In the embodiment shown, slots 140 comprise radial slots 141-145 each at a different distance from proximal end 122 of outer tubular member 120. In addition, radial slots 141-145 are coupled via a longitudinal slot 146. In this particular embodiment, radial slots 141-145 are positioned approximately 0.5 cm, 1.0 cm, 2.0 cm, 3.0 cm, and 4.0 cm from proximal end 132 of outer housing 130.

Figure 3:
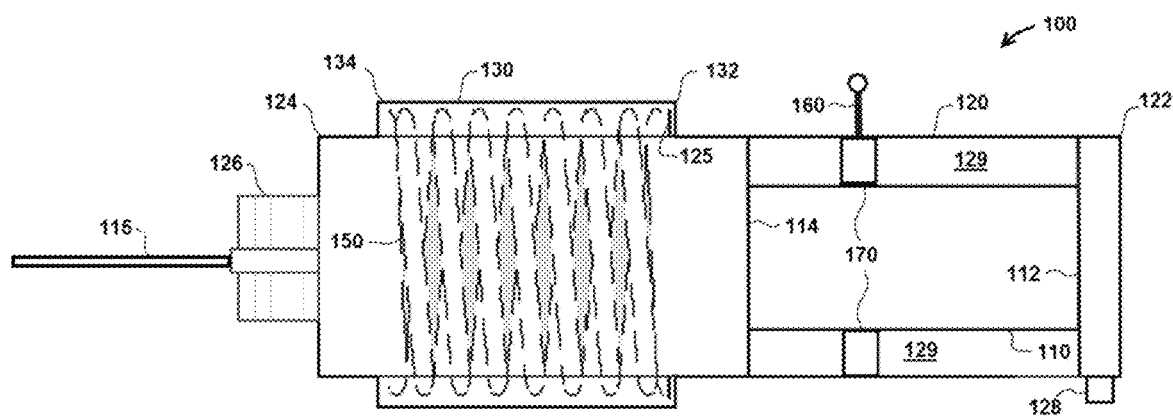
FIG. 3 is a partial section view of the embodiment of FIG. 1 in a first position.
Figure 4:
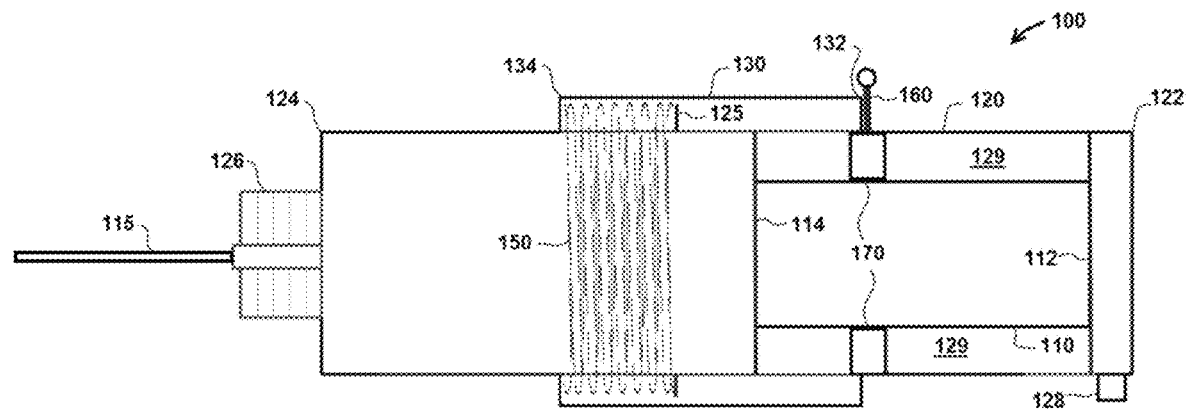
FIG. 4. is a partial section view of the embodiment of FIG. 1 in a second position.

As shown in the partial cross-section views of FIGS. 3-4, device 100 comprises a collar 170 that extends around inner tubular member 110 and is configured for axial and radial sliding engagement with inner tubular member 110. Device 100 further comprises a rod 160 that is coupled to collar 170 and extends through outer tubular member 120 through slots 140. As explained in further detail below, rod 160 can be moved into one of slots 141-145 to adjust the distance between rod 160 and proximal end 132 (of housing 130) to a desired distance. For example, if rod 160 is extending through slot 145 and the user desires to adjust the distance between rod 160 and proximal end 132 to a distance of 1.0 cm, the user can move rod 160 in a first radial direction toward longitudinal slot 146. The user can then move rod 160 along longitudinal slot 146 and into radial slot 143 in a second radial direction away from longitudinal slot 146. In certain embodiments, device 100 may comprise a motorized mechanism configured to move rod 160.

In the embodiment shown, biasing member 150 engages distal end 134 of outer housing 130 and a projection 125 that extends from outer housing 120. With biasing member 150 in an expanded configuration shown in FIG. 3, device 100 is configured so that proximal end 132 of outer housing 130 engages projection 125. During operation, a user can grip outer housing 130 and exert a force on outer tubular member 120 (e.g. in a direction from proximal end 122 toward distal end 124). The application of such a force can compress biasing member 150 and allow outer tubular member 120 to move in a longitudinal (e.g. axial) direction toward outer housing 130. Outer tubular member 120 can be moved toward outer housing 130 until rod 160 engages proximal end 132 of outer housing 130 as shown in the compressed configuration of FIG. 4. The user can control the distance that outer tubular member 120 is allowed to move toward outer housing 130 by placing rod 160 into a desired radial slot 141, 142, 143, 144, or 145. In the embodiment shown, for example, a user can control this distance to 0.5 cm, 1.0 cm, 2.0 cm, 3.0 cm or 4.0 cm by placing rod 160 into radial slot 141, 142, 143, 144, or 145, respectively.

In the embodiment shown, distal end 124 of outer tubular member 120 may comprise a coupling mechanism 126 configured to couple an instrument such as a needle 115 to distal end 124. In particular embodiments, coupling mechanism may comprise a Luer taper, including for example a Luer-Lock or a Luer-Slip configuration. Depending on the diameter of the configuration, coupling mechanism 126 can be configured so that needle 115 can be placed directly over threads at one end (with smaller diameters), or coupling mechanism 126 can have knob at the end on which needle 115 can fit (with larger diameters).

Outer tubular member 120 may further comprise a port 128 near proximal end 122 that is in fluid communication with inner tubular member 110 and coupling mechanism 126. Port 128 can be configured to be coupled to a vacuum source. In certain embodiments, port 128 can be coupled to tubing and/or a syringe or other source to provide suction or negative pressure. In the embodiment shown, a space 129 between outer tubular member 120 and inner tubular member 110 is open to external atmosphere through slots 140. However, space 129 is not in fluid communication with inner tubular member 110 or outer tubular member 120. Accordingly, a vacuum source coupled to port 128 can assist in drawing material obtained through a needle coupled to coupling mechanism 126 into the inner cavities of outer tubular member 120 and inner tubular member 110.

In particular embodiments, certain components (e.g. inner tubular member 110, outer tubular member 120, and/or outer housing 130) may be formed from a plastic or fiber material that is transparent, semitransparent, or translucent.

During certain procedures a user may place the needle (or other instrument coupled to distal end 124) against a surface of a patient while biasing mechanism 150 is in an expanded configuration. The user can grip outer housing 130 while quickly moving proximal end 122 toward outer housing 130 until rod 160 engages proximal end 132 of outer housing 130. In certain embodiments, the needle will be advanced a distance equivalent to the distance between rod 160 and proximal end 132 of outer housing 130, thereby penetrating the surface of the patient with the needle to a desired distance of penetration. The user can then withdraw the needle from the patient.

The ability to precisely control the distance that outer tubular member 120 is allowed to move relative to outer housing 130 can provide numerous benefits when performing procedures, including for instance, a fine needle aspiration (FNA). For example, the use of device 100 can allow a user to increase the speed of the instrument excursion, as well as increase the number of excursions and increase the depth of penetration. These advantages can increase the amount of tissue that is obtained by the needle and reduce the amount of blood that contaminates the sample. This can reduce failed FNA attempts and allow FNA procedures to be performed in less time. In addition, the precise depth control of device 100 can allow a user to acquire more specimen material with less blood contamination, which can sometimes obviate need for more invasive core biopsies. The straightforward operation of device 100 can also allow it to be used effectively by both experienced and inexperienced users.

It is understood that the above-described methods are merely examples of the procedures capable of being performed with exemplary embodiments of the devices disclosed herein.

All of the apparatus, devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 4,697,600
U.S. Pat. No. 4,766,907
U.S. Pat. No. 5,916,175
U.S. Pat. No. 5,951,489
U.S. Pat. No. 6,402,701
U.S. Pat. No. 7,037,276
U.S. Pat. No. 7,766,843
U.S. Pat. No. 7,927,288
U.S. Patent Publication 2002/0082518
U.S. Patent Publication 2005/0228312
U.S. Patent Publication 2013/0060160
U.S. Patent Publication 2013/0165815
U.S. Patent Publication 2013/0172777
European Patent 0983749
European Patent 0983021

The invention claimed is:

1. A device for fine needle aspiration, the device comprising:
   an inner tubular member comprising a proximal end and a distal end;
   an outer tubular member disposed around the inner tubular member, wherein the outer tubular member comprises a proximal end, a distal end, and a plurality of slots;
   an outer housing disposed around the outer tubular member, wherein the outer housing comprises a proximal end and a distal end;
   a biasing member disposed between the outer tubular member and the outer housing; and
   a rod coupled to the inner tubular member, wherein:
      the rod extends through the outer tubular member;
      the rod is configured to be moved from a first slot in the plurality of slots to a second slot in the plurality of slots;
      the first slot is a first distance from proximal end of the housing;
      the second slot is a second distance from the proximal end of the housing; and
      the biasing member is configured to bias the housing away from the rod, wherein:
         the outer tubular member comprises a projection that engages the biasing member;
         the biasing member is configured to move from an expanded configuration to a compressed configuration upon movement of the distal end of the inner tubular member toward the outer housing; and the proximal end of the housing is configured to engage the projection when the biasing member is in the expanded configuration, and wherein the proximal end of the housing is configured to engage the rod when the biasing member is in the compressed configuration.

2. The device of claim 1 wherein the rod is coupled to the inner tubular member via a collar that extends around the inner tubular member.

3. The device of claim 2 wherein the collar is configured for axial and radial sliding engagement with the inner tubular member.

4. The device of claim 1 wherein:
the outer tubular member extends a third distance from the distal end of the outer housing when the biasing member is in an expanded configuration;
the outer tubular member extends a fourth distance from the distal end of the outer housing when the biasing member is in a compressed configuration;
and the third distance is less than the fourth distance.

5. The device of claim 1 wherein the distal end of the outer tubular member comprises a coupling mechanism configured to be coupled to a needle.

6. The device of claim 5 wherein the proximal end of the outer tubular member comprises a port configured to be coupled to a vacuum source.

7. The device of claim 6 wherein the coupling mechanism and the port are in fluid communication with the outer tubular member and the inner tubular member.

8. The device of claim 1 wherein the biasing member is configured as a coil spring that extends around the outer tubular member.

9. The device of claim 1 wherein the plurality of slots comprises a plurality of radial slots each at a different distance from the proximal end of the outer tubular member and wherein the plurality of radial slots are coupled via a longitudinal slot.

10. The device of claim 9 wherein when the biasing member is in an expanded configuration the plurality of radial slots comprise:
a first slot positioned about 0.5 centimeters from the proximal end of the outer housing;
a second slot positioned about 1.0 centimeter from the proximal end of the outer housing;
a third slot positioned about 2.0 centimeters from the proximal end of the outer housing;
a fourth slot positioned about 3.0 centimeters from the proximal end of the outer housing; and
a fifth slot positioned about 4.0 centimeters from the proximal end of the outer housing.

11. A method of performing a fine needle aspiration, the method comprising:
obtaining a device comprising:
an inner tubular member comprising a proximal end and a distal end;
an outer tubular member disposed around the inner tubular member, wherein the outer tubular member comprises a proximal, a distal end, and a plurality of slots;
an outer housing disposed around the outer tubular member, wherein the outer housing comprises a proximal end and a distal end;
a biasing member disposed between the outer tubular member and the outer housing; and
a rod coupled to the inner tubular member, wherein:
the rod extends through the outer tubular member;
the rod is configured to be moved from a first slot in the plurality of slots to a second slot in the plurality of slots;
the first slot is a first distance from proximal end of the housing;
the second slot is a second distance from the proximal end of the housing; and
the biasing member is configured to bias the housing away from the rod;
coupling a needle to a coupling mechanism located near the distal end of the outer tubular member;
placing the rod in a desired slot of the plurality of slots, wherein a distance from the desired slot to the proximal end of the outer housing is equivalent to a desired distance of penetration of the needle;
placing the needle against a surface of a patient;
moving the proximal end of the outer tubular member toward the outer housing until the rod engages the proximal end of the outer housing, thereby penetrating the surface of the patient with the needle to a desired distance of penetration;
applying a vacuum to draw tissue material from the patient through the needle into the inner tubular member; and
withdrawing the needle from the patient wherein the outer tubular member comprises a projection that engages the biasing member; the biasing member is configured to move from an expanded configuration to a compressed configuration upon movement of the distal end of the inner tubular member toward the outer housing; and the proximal end of the housing is configured to engage the projection when the biasing member is in the expanded configuration, and wherein the proximal end of the housing is configured to engage the rod when the biasing member is in the compressed configuration.

12. The method of claim 11 wherein the desired distance of penetration is about 0.5 cm.

13. The method of claim 11 wherein the desired distance of penetration about 1.0 centimeter.

14. The method of claim 11 wherein the desired distance of penetration about 2.0 centimeters.

15. The method of claim 11 wherein the desired distance of penetration about 3.0 centimeters.

16. The method of claim 11 wherein the desired distance of penetration about 4.0 centimeters.

17. The method of claim 11 wherein placing the rod in the desired slot comprises:
moving the rod in a first radial direction toward a longitudinal slot;
moving the rod within the longitudinal slot toward the desired slot; and
moving the rod in a second radial direction into the desired slot.

18. The method of claim 11 wherein moving the proximal end of the outer tubular member toward the outer housing comprises overcoming a force exerted by the biasing mechanism on the outer housing and the outer tubular member.

* * * * *